US011660199B2

(12) United States Patent
Heggs et al.

(10) Patent No.: US 11,660,199 B2
(45) Date of Patent: May 30, 2023

(54) MODULAR KNEE AUGMENT CONES

(71) Applicant: Encore Medical, LP, Austin, TX (US)

(72) Inventors: Jesse Heggs, Pflugerville, TX (US); Alex Drew, Austin, TX (US); John Green, Austin, TX (US)

(73) Assignee: ENCORE MEDICAL, L.P., Austin, TX (US)

( * ) Notice: Subject to any disclaimer, the term of this patent is extended or adjusted under 35 U.S.C. 154(b) by 274 days.

(21) Appl. No.: 17/161,048

(22) Filed: Jan. 28, 2021

(65) Prior Publication Data

US 2021/0228366 A1     Jul. 29, 2021

Related U.S. Application Data

(60) Provisional application No. 62/967,342, filed on Jan. 29, 2020.

(51) Int. Cl.
*A61F 2/38* (2006.01)
*A61F 2/30* (2006.01)

(52) U.S. Cl.
CPC .......... *A61F 2/389* (2013.01); *A61F 2/30771* (2013.01); *A61F 2002/30011* (2013.01); *A61F 2002/30205* (2013.01); *A61F 2002/30448* (2013.01); *A61F 2002/30881* (2013.01)

(58) Field of Classification Search
CPC ........ A61F 2/30734; A61F 2002/30736; A61F 2002/30205; A61F 2002/30881; A61F 2/30767; A61F 2002/30383; A61F 2002/30403; A61F 2002/3092; A61F 2002/30401; A61F 2002/30398
See application file for complete search history.

(56) References Cited

U.S. PATENT DOCUMENTS 7,291,174 B2   11/2007   German et al.
8,366,782 B2   2/2013    Wright
8,382,849 B2   2/2013    Thomas
(Continued)

FOREIGN PATENT DOCUMENTS

WO   WO-2016183439 A1 *  11/2016   ......... A61F 2/30734
WO   WO-2016183446 A1 *  11/2016   ............. A61B 17/72

OTHER PUBLICATIONS

International Search Report and Written Opinion issued in application No. PCT/US2021/015517, dated May 6, 2021.

*Primary Examiner* — Javier G Blanco
(74) *Attorney, Agent, or Firm* — Knobbe, Martens, Olson & Bear LLP

(57) ABSTRACT

A modular augment cone system and methods of implanting the modular augment cone system. The system includes a main body cone a first cutout in the cone wall, and including a proximal end, a distal end, and a cone wall extending between the proximal and distal ends. A portion of the cone wall proximal to the first cutout includes an attachment feature. A first augment cone is positionable in the first cutout, the first augment cone including an attachment feature configured to mate with the attachment feature of the cone wall to attach the first augment cone into the first cutout. The main body cone can include a second cutout in the cone wall. In such systems, the modular augment cone system can include a second augment cone configured to mate with an attachment feature of the cone wall to attach the second augment cone into the second cutout.

10 Claims, 16 Drawing Sheets

(56) References Cited

U.S. PATENT DOCUMENTS

| | | |
|---|---|---|
| 8,506,645 B2 | 8/2013 | Blaylock et al. |
| 9,517,138 B2 | 12/2016 | Zimmer et al. |
| 9,526,513 B2 | 12/2016 | Collazo et al. |
| 9,688,758 B2 | 6/2017 | Wranik et al. |
| 10,123,215 B2 | 11/2018 | Zhang |
| 10,201,426 B2 | 2/2019 | Hanssen et al. |
| 10,265,083 B2 | 4/2019 | Servidio et al. |
| 10,335,171 B2 | 7/2019 | Collazo et al. |
| 2008/0167722 A1* | 7/2008 | Metzger .............. A61F 2/30721 623/20.29 |
| 2014/0277528 A1* | 9/2014 | Mines .................... A61F 2/389 623/20.14 |
| 2016/0058560 A1 | 3/2016 | Blaylock et al. |
| 2016/0278925 A1 | 9/2016 | Roby |
| 2018/0008416 A1 | 1/2018 | Vergari |
| 2019/0015215 A1* | 1/2019 | Marlow .................... A61F 2/38 |

* cited by examiner

MODULAR KNEE AUGMENT CONES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57 for all purposes and for all that they contain.

TECHNICAL FIELD

The present invention relates to cones and augments used in knee revision surgery. More particularly, the present application describes a modular knee augment cone system having a main body cone and an augment which can be mated together to form an asymmetric revision cone.

BACKGROUND

A revision knee replacement surgery is a procedure that is performed to replace a knee implant that is no longer functioning properly. Various cone augments are implanted into patients during surgical procedures on the knee, e.g., to accept a tibial implant. The cones needed for such procedures may be symmetric cones or asymmetric cones. The asymmetric cones may be left asymmetric, right asymmetric, or dual asymmetric, based on the positioning of the augment on the main body portion of the cone. The augment cones are expensive. In order to ensure the correct augment cones are on hand for use during surgeries as needed, a variety of different types of augment cones must be kept in inventory. Accordingly, to save costs and to simplify the supply chain, it would be beneficial to have a single augment cone system that is can be used for most, if not all, procedures.

SUMMARY

The invention is defined by the independent claims. The dependent claims concern optional features of some embodiments of the invention. The systems, methods, and devices described herein each have several aspects, no single one of which is solely responsible for its desirable attributes. Without limiting the scope of this disclosure, several non-limiting features will now be discussed briefly.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

One innovation includes a modular augment cone system, comprising, for example, a main body cone including a proximal end, a distal end, and a cone wall extending between the proximal end and the distal end, the main body cone further including a first cutout in the cone wall, wherein a portion of the cone wall proximal to the first cutout includes a cone wall attachment feature, and a first augment cone positionable in the first cutout, the first augment cone including an augment attachment feature configured to mate with the cone wall attachment feature to attach the first augment cone into the first cutout.

The modular augment cone system can include a number of different embodiments having different aspects or features, some of which are discussed here. However, the innovation is not limited to different embodiments, or different features that are discussed here. Also, the features that are disclosed herein may be included in various embodiments of a modular augment system whether or not they are explicitly described as being included in a particular embodiment, unless explicitly indicated otherwise or indicated by context of the features. For example, in some embodiments, an exterior surface of the first augment cone extends away from a center portion of the main body cone when the first augment cone is positioned in the first cutout. In some embodiments, the main body cone further comprises a second cutout in the cone wall and a portion of the cone wall proximal to the second cutout includes cone wall attachment structure. In some embodiments, the modular augment cone system further comprises a second augment cone positionable in the second cutout, the second augment cone including augment attachment structure configured to mate with the cone wall attachment structure to attach the second augment cone into the second cutout.

In some embodiments of a modular augment cone system, the cone wall of the main body cone includes an exterior surface comprising a porous coating. In some embodiments, the cone wall of the main body cone includes an exterior surface comprising a porous coating. In some embodiments, the porous coating extends to the distal end of the main body cone. In some embodiments the porous coating extends to the proximal end of the main body cone. In some embodiments the porous coating extends to the proximal end and the distal end of the main body cone. In some embodiments, the main body cone further comprises a distal ring structure positioned circumferentially at the distal end of the main body cone on the exterior surface of the cone wall, and wherein the porous coating extends to the distal ring structure. In some embodiments, the main body cone further comprises a proximal ring structure positioned circumferentially at the proximal end of the main body cone on the exterior surface of the cone wall, and wherein the porous coating extends to the proximal ring structure. In some embodiments, the main body cone further comprises a proximal ring structure positioned circumferentially at the proximal end of the main body cone on the exterior surface of the cone wall, and a distal ring structure positioned circumferentially at the distal end of the main body cone on the exterior surface of the cone wall, and wherein the porous coating extends between the proximal ring structure and the distal ring structure. In some embodiments, the first augment cone includes an exterior surface comprising a porous coating.

In some embodiments of a modular augment cone system, the main body cone comprises one or more ribs positioned circumferentially on an interior wall of the main body cone, the one or more ribs providing surfaces that allow an adhesive to purchase against. In some embodiments, the cone wall attachment feature comprises a slot. In some embodiments, the attachment feature on the augment comprises an extended portion that fits into the slot of the cone wall attachment feature. In some embodiments, the attachment feature on the augment comprises a slot. In some embodiments, the cone wall attachment feature comprises a slot. In some embodiments, the cone wall attachment feature comprises an extended portion that fits into the slot of the attachment feature on the augment.

In some embodiments of a modular augment cone system, the circumference of the proximal end of the main body cone is greater than the circumference of the distal end of the main body cone. In some embodiments, the first cutout is positioned opposite of the second cutout in the cone wall. In some embodiments, the first cutout and the second cutout are positioned in the cone wall such that a portion of the cone wall between a first edge of the first cutout and an adjacent first edge of the second cutout is larger than a portion of the cone wall between the second edge of the first cutout and an adjacent second edge of the second cutout. In some embodiments, the main body cone is a cross section of the main body cone parallel to a longitudinal axis of the main body cone is substantially circular. In some embodiments, the first cutout extends from the proximal end of the main body cone towards the distal end of the main body cone but does not reach the distal end of the main body cone. In some embodiments, the first cutout extends from the distal end of the main body cone towards the proximal end of the main body cone but does not reach the proximal end of the main body cone. In some embodiments, a width w dimension of the first cutout along the proximal end of the main body cone is between about 16 mm and about 25 mm. In some embodiments, a length/dimension of the first cutout along the extent of the first cutout from the proximal end of the main body cone towards the distal end of the main body cone is between about 14 mm and 24 mm.

Another innovation includes a modular augment cone system, including a main body cone including a proximal end, a distal end, and a cone wall extending between the proximal end and the distal end, the main body cone further including a first cutout in the cone wall structured to receive an augment cone, wherein a portion of the cone wall proximal to the first cutout includes a cone wall attachment feature.

Another innovation includes a modular augment cone system, including an augment cone configured to be positioned in a cutout in a wall of a main body cone, the augment cone including an augment attachment feature configured to mate with an attachment feature on the wall of the main body cone to attach the augment cone to the wall and cover the cutout in the wall of the main body cone. In some embodiments, the main body cone, the main body cone having a proximal end, a distal end, and a cone wall extending between the proximal end and the distal end, the main body cone further including the cutout in the cone wall, wherein a portion of the cone wall proximal to the first cutout includes an attachment feature configured to mate with the attachment feature of the augment cone.

Another innovation includes a method of using a modular augment cone system, the method including positioning a main body cone as described herein into a patient, and placing the first augment cone into the first cutout.

Another innovation includes a method of using a modular augment cone system, the method including positioning a main body cone into a patient, and placing the first augment cone into the first cutout.

Another innovation includes a method of using a modular augment cone system, the method including providing a modular augment cone system as described herein, positioning and connecting an augment cone into a first cutout of the main body cone, and implanting the main body cone with the connected augment cone. For example, implanting the main body cone with the connected augment cone into a portion of a knee of a patient.

Another innovation includes a method of implanting a modular augment cone system, the method comprising assembling the modular augment cone system of claim 1 by placing the first augment cone into the first cutout, and implanting the modular augment cone system comprising the main body cone and the first augment cone into a prepared space.

Another innovation includes a method of implanting a modular augment cone system, the method comprising providing the modular augment cone system, and positioning a first augment cone into a first cutout of the main body cone.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1A illustrates the main body portion (or "main body cone") of a modular symmetric cone having a plurality of cutouts in opposite walls of the main body portion, the cutouts each configured to receive an augment cone (an "augment"). The main body portion of a modular symmetric cone may be referred to herein as a "main body cone" or "main body portion" for ease of reference.

FIG. 10 also illustrates that in this example, the main body cone and the first and second arguments include porous lattice surfaces on exterior surfaces of these components.

DETAILED DESCRIPTION

Overview

Figure 1A:
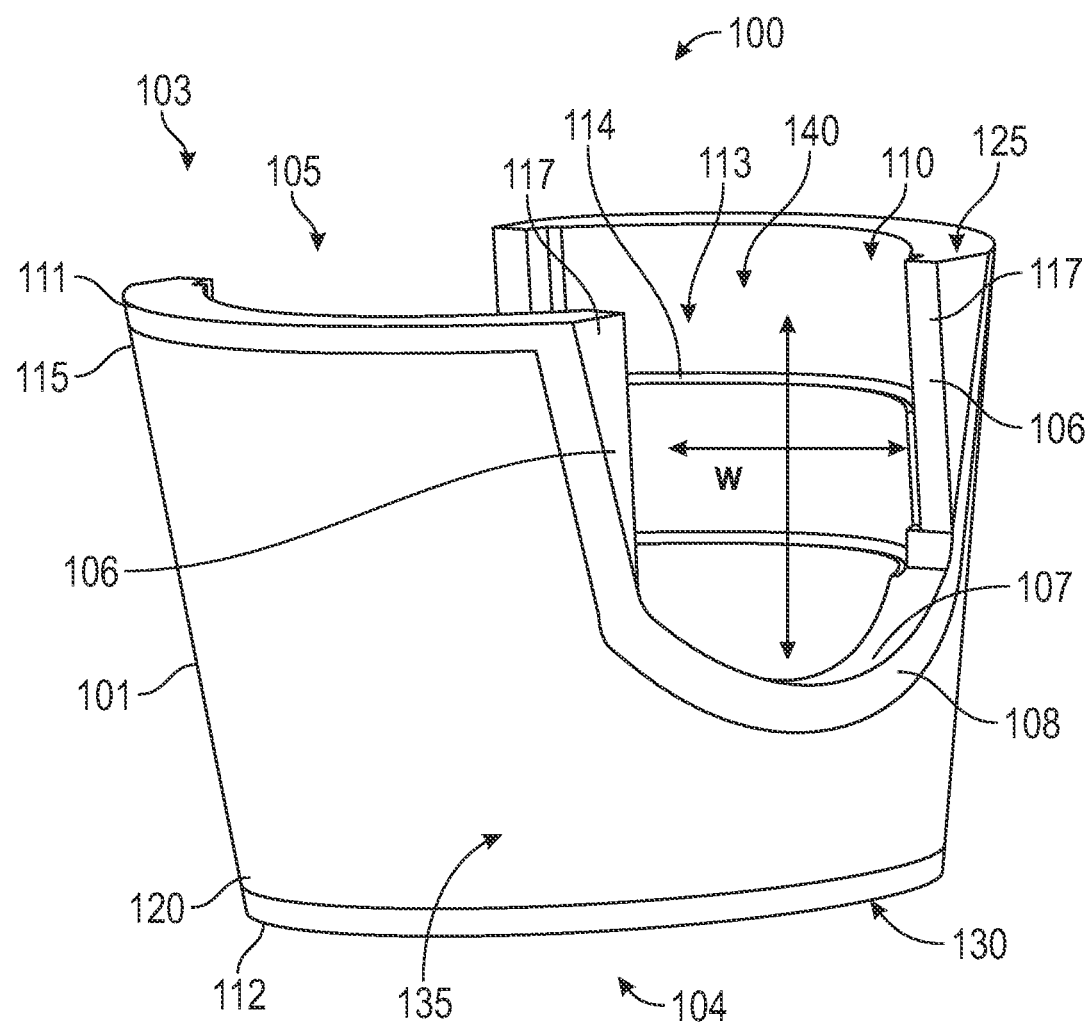
FIG. 1A is a side perspective view illustrating an example of an embodiment of a symmetric main body cone of a modular augment cone system. For example, of a modular knee augment cone system.

This application relates to a modular augment cone system, which can be used for example, as an implant in a patient's knee. In an example, an application for the modular augment cone system described herein can be used in revision knee procedures to provide support and to fill the void left by the primary implant. In some embodiments, a femoral cone can be used as well. The modular augment cone system includes a main body cone and an augment cone ("augment") which can be mated with the main body cone by positioning the augment in a cutout of a wall of the main body cone to create an asymmetric cone. The general shape of the main body cone can be a frustum cone. In an example, the frustum cone-shaped main body cone has a first diameter on a proximal end and a second diameter on a distal end, the first diameter being larger than the second diameter. In some embodiments, the first diameter is between 25 mm and 60 mm. In some embodiments, the first diameter is between 32 mm and 50 mm. In some embodiments, the second diameter is between 20 mm and 55 mm. In some embodiments, the second diameter is between 25 mm and 40 mm. The main body cone can be symmetric in its general structure, e.g., the portions of its structure not involving the cutouts and the augment cones. The edges of the main body cone that are mated with the augment at the cutout include an attachment feature, which may include one or more structural configurations (e.g., one or more of a slot, groove, protrusion, dovetail, post, divot, teeth, ball, or post, and the like). In some embodiments, the main body cone is medial symmetric, or lateral symmetric. The internal diameter of the main body cone can be wide enough to accommodate an implant as well as an offset stem.

In some embodiments, the main body cone described herein is a trial cone. The trial cone can be made from metal or plastic. However, some embodiments of a trial cone will not have a permanent locking feature (where embodiments of an implantable main body cone have a permanent locking feature to lock the augment into the main body cone). Instead, the trail cone may include a temporary locking feature, for example, a screw, a ball detent/post and divot, or snap tabs. If the distal force is deemed acceptable for trialing, the trail main body cone and augment may not have a locking feature, e.g., a distal locking feature.

The augment has an open upper ("proximal") portion and a lower ("distal") generally hemispherical-shaped portion. The edges of the augment that are mated with the main body cone at the cutout also includes an attachment feature (e.g., one or more of a slot, groove, protrusion, dovetail, post, divot, teeth, ball, or post, and the like) that corresponds with the attachment feature of the main body cone such that the augment can be securely positioned into the cutout, mated to the main body cone. The attachment features of the main body cone and the augment may include one or more structures, and may include a locking device (e.g., a pin, screw, or other fastener). In some embodiments, the fixation for the asymmetric augment for the cone can be a slot which provides no distal/proximal securement or a variety of locking mechanisms. In other embodiments, the fixation for the augment in the main body portion may be accomplished by one of a variety of locking mechanisms which in include but are not limited to dovetail, leaf spring, locking tabs, spring loaded ball/post and divot, a screw, a pin, or ratchet teeth.

Figure 6:
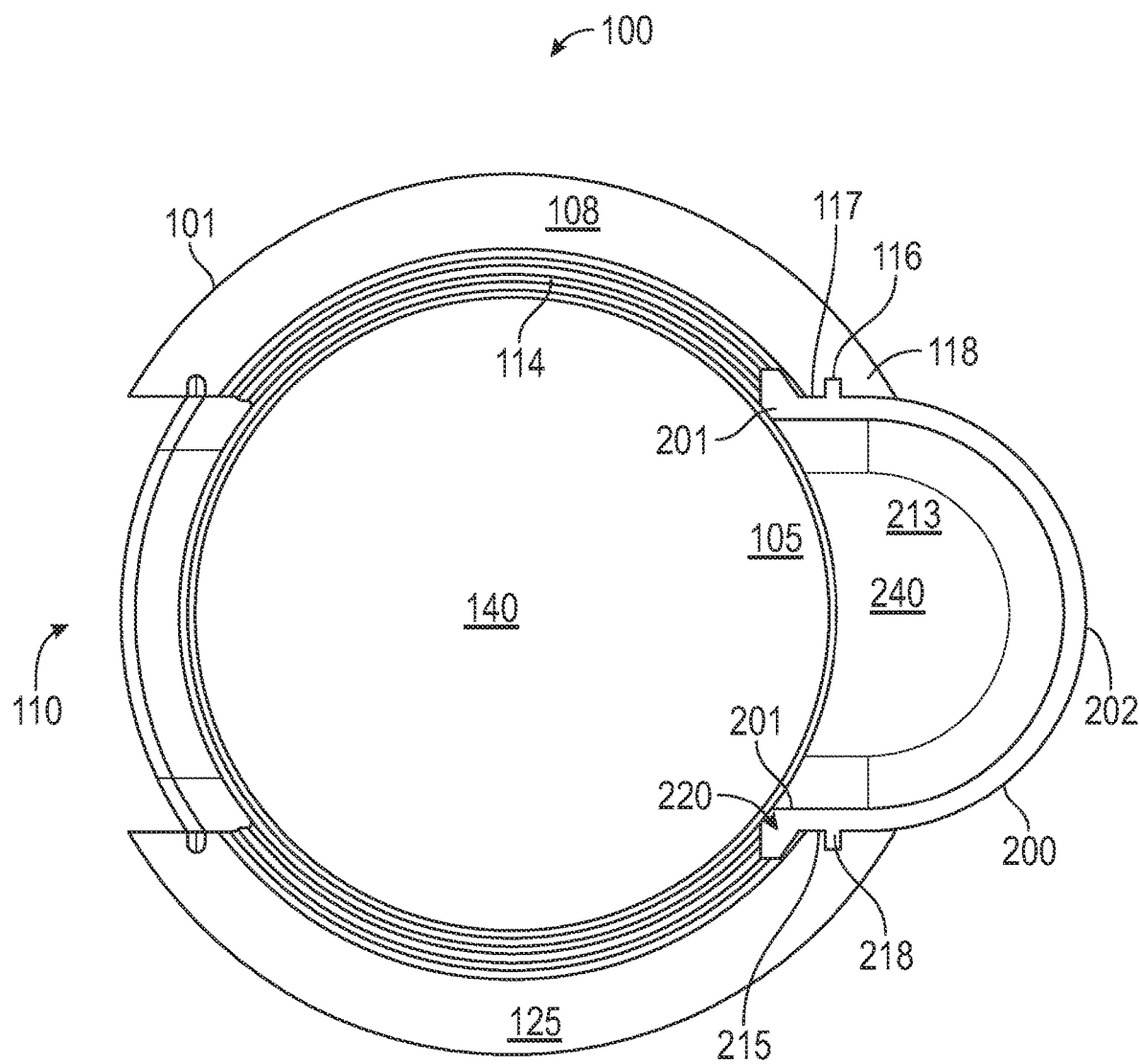
FIG. 6 is a top ("proximal") plan view illustrating another example of a modular knee augment cone system having in augment positioned in a first cutout of the main body cone.

When an augment is positioned in a cutout of the main body cone, an asymmetric revision cone is formed. That is, an augment can be mated with the symmetric main body cone to create an asymmetric cone. The main body cone includes a cavity. The augment also includes a cavity partially surrounded by an augment interior surface/wall. The augment, when mated with the main body cone, covers the cutout, and extends from the main body cone such that the augment cavity and the main body cone cavity together form a larger cavity surrounded by structure of the main body cone and the augment cone (see for example, FIG. 6 showing the cavity 140 of the main body cone and cavity 240 of the augment joined to form a larger cavity).

The main body cone can be described as having an "upper" or "proximal" end (that when implanted is positioned proximal to the patient's heart) and as having a "lower" or "distal" end (which is positioned distal from the patient's heart when implanted). The main body cone includes at least one cutout (or gap) in the wall of the main body cone. The portion of the wall around each cutout includes an attachment feature that is configured to receive and attach to an augment. In some embodiments, the main body cone has one cutout. In some embodiments, the main body cone has two cutouts. In some embodiments, the main body cone has three or more cutouts. The cutouts may sometimes be referred to as "slots" in reference to the functionality that they may enable. That is, the attachment features of the main body cone and the augment can be configured to allow an augment cone to be positioned in the cutout by sliding the augment from the proximal end of the main body portion into the wall of the main body. The main body portion can have structure that allows grooves in opposite sides of the augment cone to be fitted onto the wall of the main body cone, and allows the augment cone to be slid into a cutout, positioning the augment into the cutout such that the augment mates with in the main body portion. In an example, when the augment is positioned in a cutout, a proximal end (e.g., a surface) of the augment is aligned with the proximal edge (or surface) of the main body portion. That is, the proximal end of the augment may be aligned with a plane that is also aligned with the proximal end of the main body cone when the augment is seated in the cutout.

In an embodiment, a main body cone includes two cutouts, each cutout can accept an augment cone positioned therein. In some embodiments, the two cutouts can be configured in the main body portion wall directly opposite each other (e.g., on opposite sides of the main body portion) as illustrated, for example, in FIG. 6. In such examples, centers of the two cutouts are aligned 180 degrees apart. In some embodiments, the two cutouts can be configured in the main body portion wall opposite each other but they may not be directly opposite each other. For example, the first cutout and the second cutout can be positioned in the cone wall such that a portion of the cone wall between a first edge of the first cutout and an adjacent first edge of the second cutout is larger than a portion of the cone wall between the second edge of the first cutout and an adjacent second edge of the second cutout. In such examples, the centers of the two cutouts are not 180 degrees separated. That is, the cutout center separation angle (as illustrated in FIG. 6) is not 180°. In various embodiments of a main body cone having two cutouts, a cutout center separation angle is 1°, 2°, 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, 30°, 31°, 32°, 33°, 34°, 35°, 36°, 37°, 38°, 39°, 40°, 41°, 42°, 43°, 44°, 45°, 46°, 47°, 48°, 49°, 50°, 51°, 52°, 53°, 54°, 55°, 56°, 57°, 58°, 59°, 60°, 61°, 62°, 63°, 64°, 65°, 66°, 67°, 68°, 69°, 70°, 71°, 72°, 73°, 74°, 75°, 76°, 77°, 78°, 79°, 80°, 81°, 82°, 83°, 84°, 85°, 86°, 87°, 88°, 89°, 90°, 91°, 92°, 93°, 94°, 95°, 96°, 97°, 98°, 99°, 100°, 101°, 102°, 103°, 104°, 105°, 106°, 107°, 108°, 109°, 110°, 111°, 112°, 113°, 114°, 115°, 116°, 117°, 118°, 119°, 120°, 121°, 122°, 123°, 124°, 125°, 126°, 127°, 128°, 129°, 130°, 131°, 132°, 133°, 134°, 135°, 136°, 137°, 138°, 139°, 140°, 141°, 142°, 143°, 144°, 145°, 146°, 147°, 148°, 149°, 150°, 151°, 152°, 153°, 154°, 155°, 156°, 157°, 158°, 159°, 160°, 161°, 162°, 163°, 164°, 165°, 166°, 167°, 168°, 169°, 170°, 171°, 172°, 173°, 174°, 175°, 176°, 177°, 178°, or 179°, plus or minus 0.5 degrees.

Various embodiments of the main body portion, and/or the augment, the internal surface of the main body cone can include one or more axially-aligned ribs for rotational fixation for cement. The axially-aligned ribs allow the cement to have purchase against a surface which is not curved around the center axis which provides resistance against a rotational force around the axis of the main body cone. In some embodiments, preparation for using the implant can include an over ream on the stem reamer for the main body, and then an offset jig with an augment reamer for the augment cone.

In some embodiments, outer surfaces (i.e., facing away from the cavity) of the main body cone and augment include a surface structure to facilitate bone in-growth. In some embodiments, the surface structure includes $P^2$, a proprietary titanium porous coating by DJO Surgical. An advantage of $P^2$ is that the non-spherical bead of the coating itself is also porous, thus giving it its name, P-Squared ($P^2$). Consisting of variability in pore sizes, very similar to a "lava rock" type of structure, $P^2$ aids in the apposition of bone for superior in-growth results. In some embodiments, the surface structure can be another type of porous of rough coating. In some embodiments, the surface structure is 3D printed to generate a porous lattice surface. In some embodiments, the porous coating is a consistent depth on the outside surface (e.g., an outside surface of the main body cone and/or an outside surface of a segment cone). Depending on the manufacturing method, there may or may not be upper (proximal) and lower (distal) rings on the exterior surface of main body cone to capture, or limit, the porous coating. There may be an upper ring, lower ring, both, or none depending on manufacturing ease. In some embodiments, the main body cone does not include either one or more of the upper or lower rings, and the coating can be an all-around coating.

In some embodiments, the surface structure is generated using traditional subtractive manufacturing (e.g., removing material from an exterior surface, or surface coating, of the main body cone and/or augment cone).

Terms

In order to facilitate an understanding of the systems and methods discussed herein, a number of terms are defined below. The terms defined below, as well as other terms used herein, should be construed to include the provided definitions, the ordinary and customary meaning of the terms, and/or any other implied meaning for the respective terms. Thus, the definitions below do not limit the meaning of these terms, but only provide exemplary definitions.

Figure 2:
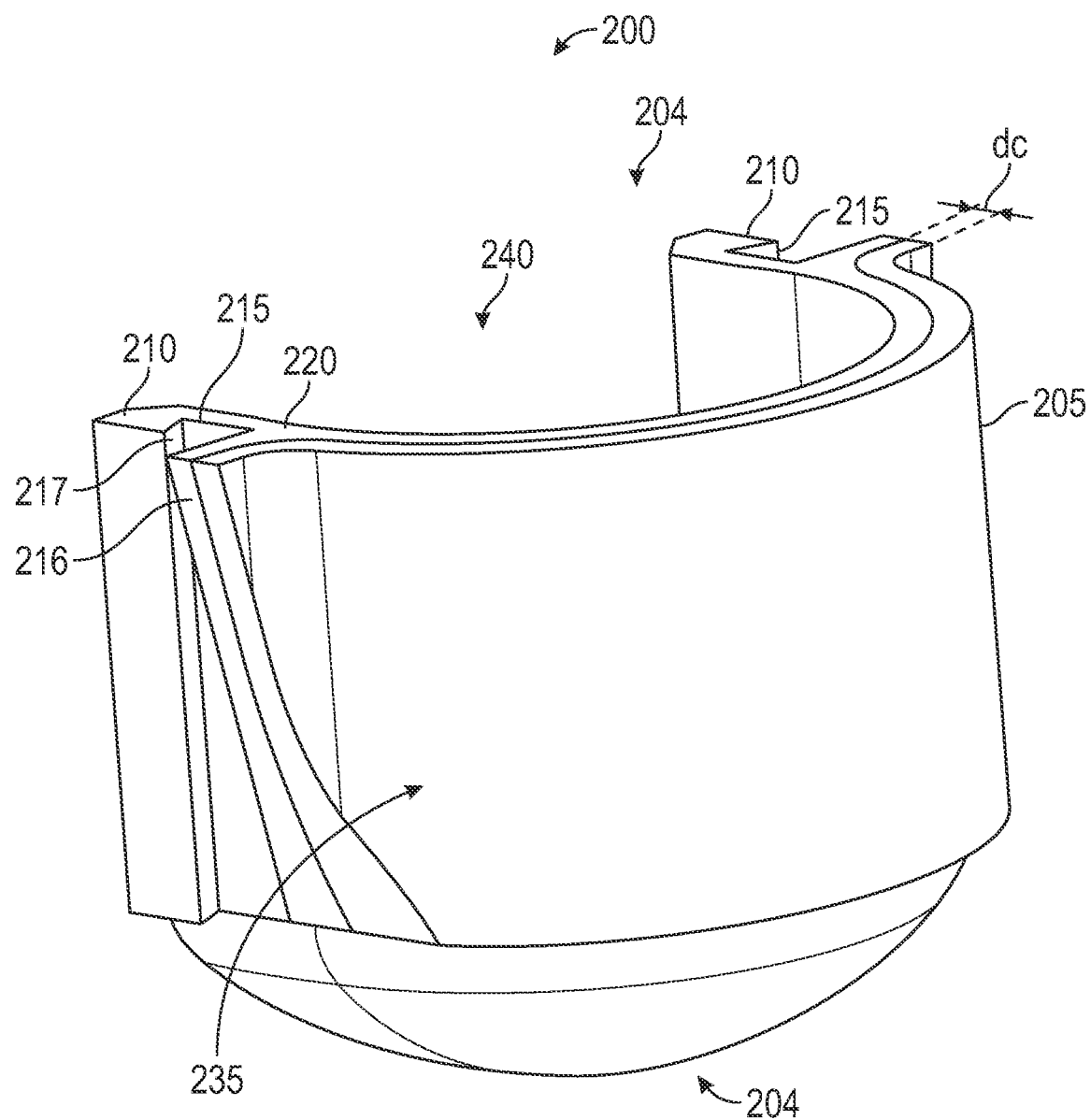
FIG. 2 is a perspective view that illustrates an example of an augment that is configured to be positioned in a cutout of the main body cone illustrated in FIG. 1A. The augment includes structure near its edge portions that fits into, and/or against, corresponding structure along edge portions of the cutout to allow the augment to seat into the main body cone and be attached to the main body cone in the cutout.

Augment cone: a component of a modular augment cone system, an example of which is illustrated in FIG. 2. The augment cone is positionable into an opening (or cutout) of a main body cone, and can be attached to the main body cone by corresponding attachment structure of the augment cone and the main body cone. The augment cone includes a cavity which is partially surrounded by the augment cone structure. In use, the augment is attached to the main body cone and may be locked into place before the main body cone/augment cone system is implanted in a patient.

Main body cone: a component of a modular augment cone system, an example of which is illustrated in FIG. 1A. The main body cone is frustum cone-shaped, and structured to receive an implant (e.g., a tibial implant). The main body cone includes an opening (or cutout) that is configured to receive an augment cone. The main body cone may have one or more cutouts, and the main body cone also includes a cavity which is partially surrounded by main body cone structure. When the augment cone is attached to the main body cone, the cavity of the augment cone is contiguous with the cavity of the main body cone, forming a larger cavity than the cavity of the main body cone.

Figure 10:
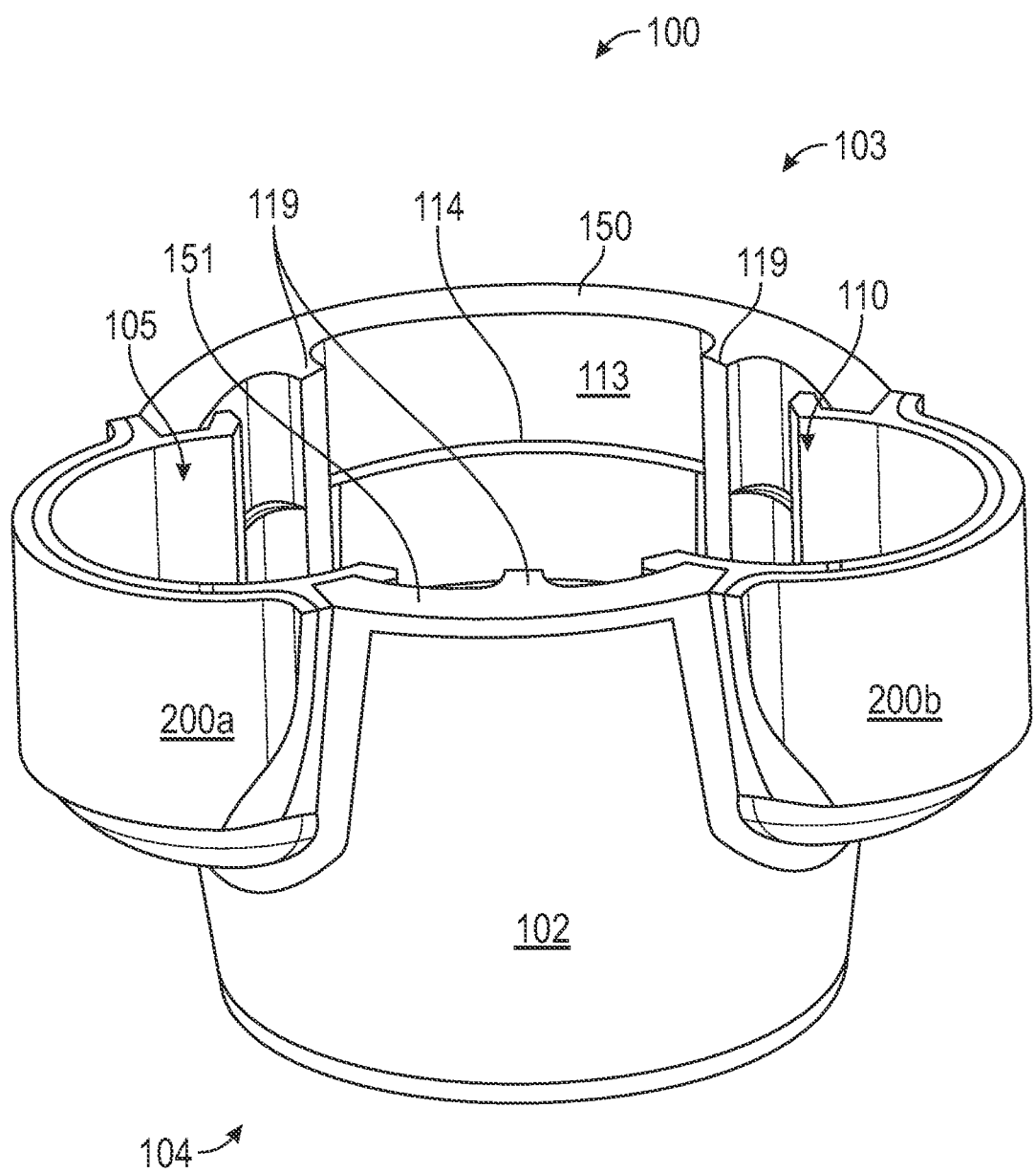
FIG. 10 is a perspective view illustrating an example of a main body cone, and a first augment positioned in a first cutout of the main body cone and a second augment positioned in a second cutout of the main body cone.

Modular augment cone system: a system that includes a main body cone and one or more augment cones, an example of which is illustrated in FIG. 10. The modular augment cone system may include other components that are attached to the main body cone.

P²: is a new proprietary Titanium Porous coating by DJO Surgical, and the first porous coating in the world wherein the non-spherical bead itself is also porous—giving it its name, P-Squared (P²). Consisting of variability in pore sizes, very similar to a "lava rock" type of structure, P² aids in the apposition of bone for superior in-growth results. P² consists of two ranges of pore sizes—Inter- and Intra-bead. This variability in pore size range is what gives P² a distinct advantage in accommodating rapid bone in-growth. In an example of Inter-bead pore size, the pore size between each non-spherical bead equals 200-525 microns (μm). In an example of Intra-bead pore size, the pore size within each non-spherical bead equals 25-65 microns (μm).

List of Certain Components

Figure 1B:
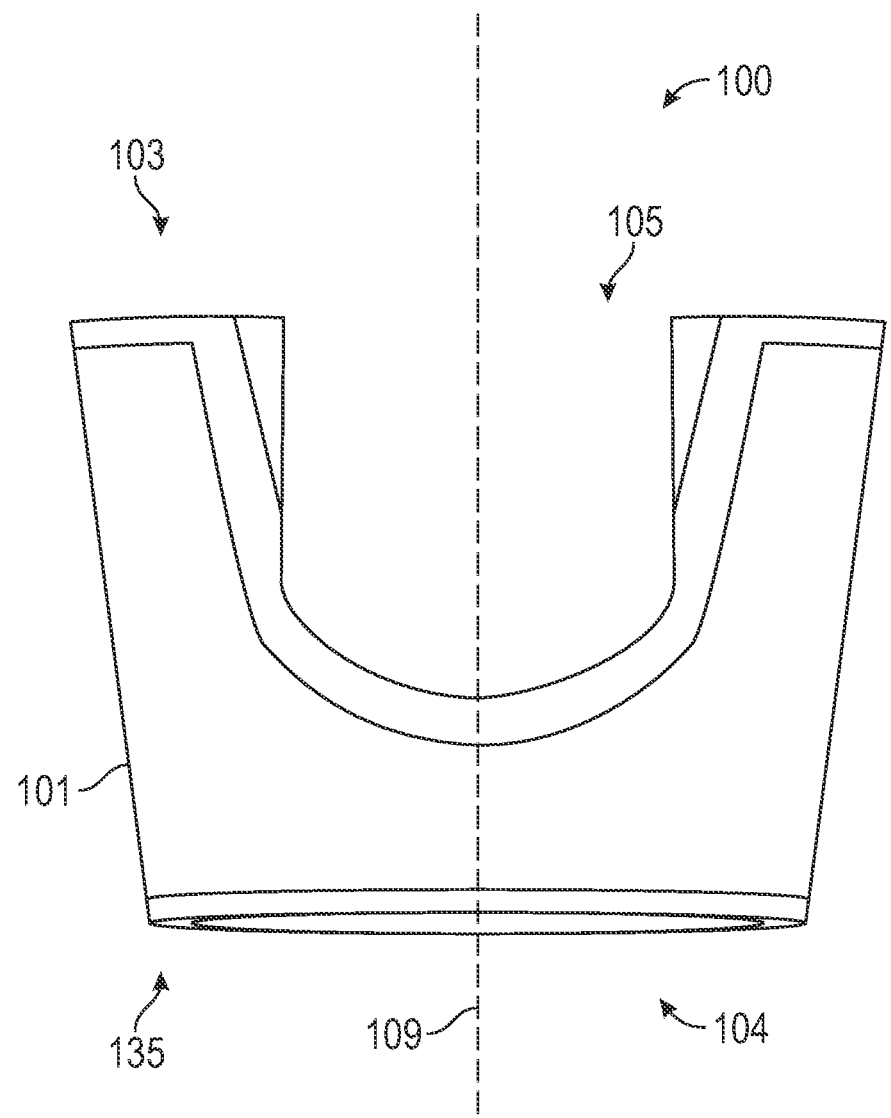
FIG. 1B is a side elevation view illustrating the main body cone of FIG. 1A, showing a longitudinal axis of the main body cone.
Figure 1C:
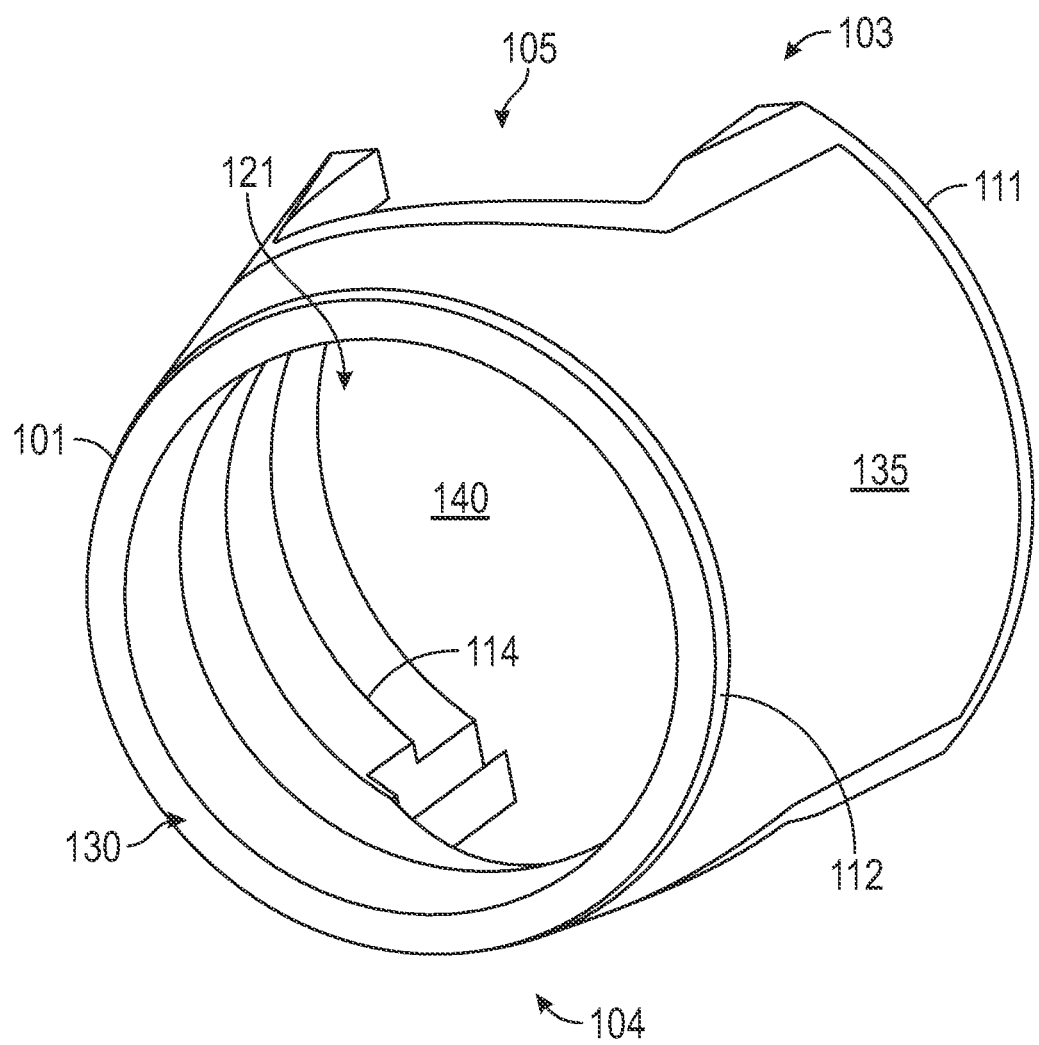
FIG. 1C is a bottom perspective view of the main body cone of FIG. 1A illustrating the circular planar lower surface on the distal end of the main body cone.

The following is a list of certain components that are described and enumerated in this disclosure in reference to the above-listed figures. However, any aspect of the devices illustrated in the figures, whether or not named out separately herein, can form a portion of various embodiments of the invention and may provide basis for claim limitation relating to such aspects, with or without additional description. The enumerated components include:

A angle of inward taper of wall
l length of cutout
w width of cutout
dc depth of bone growth coating
100 modular knee augment cone system
101 symmetric main body cone
102 asymmetric main body cone
103 proximal end
104 distal end
105 first cutout
106 cutout lateral edge
107 cutout lower edge
108 wall of main body cone
109 longitudinal axis of main body cone
110 second cutout
111 upper ring
112 lower ring
113 interior wall main body cone
114 cement mantel step/circumferential rib on interior wall main body cone
115 upper portion of main body cone
116 groove in wall on edge of cutout
117 cone wall attachment feature
118 outside portion of cone wall attachment feature
119 axially-aligned rib
120 lower portion of main body cone
121 aperture in distal end of main body cone
125 upper surface
130 lower surface
135 exterior surface main body cone/bone growth surface
140 cavity
150 large (long) wall of asymmetric main body cone
151 small (short) wall of asymmetric main body cone
200 augment cone
201 inside edge of augment cone
202 outside end
203 proximal end
204 distal end
205 exterior wall of augment cone
210 edge portion
213 interior wall augment cone
215 groove/augment attachment feature
216 attachment feature
217 attachment feature
218 protrusion of augment attachment feature
220 upper surface augment cone
235 bone growth surface portion of augment cone
240 cavity of augment cone
260 tibial implant
262 tibial implant keel
264 upper portion tibial implant
266 lower portion tibial implant
268 bottom surface of tibial implant Examples of Knee Augment Cone Systems and Methods FIGS. 1A-1C illustrate an example of an embodiment of a modular knee augment cone system. FIG. 1A is a side perspective view illustrating an example of an embodiment of a symmetric main body cone of a modular knee augment cone system. The main body portion of the modular symmetric cone may be referred to herein as a "main body cone" or "main body portion" for ease of reference. FIG. 1B is a side elevation view illustrating the main body cone 101 of FIG. 1A, showing a longitudinal axis 109 of the main body cone 101. FIG. 1C is a bottom perspective view of the main body cone 101 of FIG. 1A, illustrating a circular planar lower surface 130 on the distal end 104 of the main body cone 101. The view of FIG. 1C also illustrates a circular aperture 121 in the distal end 104 of the main body cone surrounded by the lower surface 130.

The main body cone 101 include cutouts 105, 110 in opposite portions of the wall 108 of the main body cone 101. Although the portions of the wall 108 that forms an opening may be referred to a "cutout" 105, 110, the term "cutout" as used herein is not meant to require that these gaps in the walls are formed by removing or cutting away material of the main body cone wall, although they may be formed at least in part that way. Rather, the term "cutout" is used herein to, for example, refer to a portion of the main body cone wall that includes a gap configured to receive an augment cone, regardless of how it was formed. The main body cone 101 partially surrounds a portion of a cavity 140. Each of the cutouts 105, 110 are configured to receive an augment cone (for example, augment cone 200 in FIG. 2).

In the example illustrated in FIG. 1A, the main body portion 101 is frustum cone-shaped, and is in this example symmetrical. In some embodiments, an upper portion 115 of the main body cone 101 can have a larger diameter than a lower portion 120 of the main body cone 101. The one or more cutouts 105, 110 extend from an upper surface 125 of the main body portion 101 towards a lower surface 130 of main body 101. Each cutout can have a width w and a length l. The dimensions of the cutout can be based at least in part on the size of the main body cone, and/or the size of an implant used with the main body cone 101. In some embodiments, a width w dimension of the first cutout along the proximal end of the main body cone is between about 16 mm and about 25 mm. In some embodiments, the width w dimension of the first cutout along the proximal end of the main body cone is 12 mm, 13, mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, or 29 mm, plus or minus 0.5 mm. In some embodiments, a length/dimension of the first cutout along the extent of the first cutout from the proximal end of the main body cone towards the distal end of the main body cone is between about 14 mm and 24 mm. In some embodiments, the length l dimension of the first cutout along the proximal end of the main body cone is 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, or 31 mm, plus or minus 0.5 mm. In this example, the cutouts 105, 110 do not extend the entire length of the wall 108 but instead extend into the wall 108 from the upper surface 125 to a length of about more than half the height of the main body portion wall 108. Other examples may differ, and the cutout 105, 110 may extend further than illustrated example, or not as far as illustrated example.

FIG. 1A also illustrates a bone growth surface portion surface structure 135 on the outside surface of the main body portion (illustrated as a darker surface) that is made to facilitate bone growth into the surface to hold the surface in place. In some examples, the surface structure 135 is $P^2$. In some examples, the surface is formed on the main body cone with an additive manufacturing process, for example, with a 3-D printer. In some example, the surface structure 135 is formed with a subtractive manufacturing process. In this example, the main body cone 101 includes an upper ring 111 that extends circumferentially around the proximal end 103 of the main body cone, and a lower ring 112 that extends circumferentially around the distal end 104 of the main body cone. The surface structure 135 extends across the exterior surface of the main body cone between the upper ring 111 and the lower ring 112. In The cutout lateral edges 106 and the cutout lower edge 107, may not include the surface structure 135 because such edges 106, 107 allow the augment cone to slide into the cutout, and are not exposed when an augment is seated in the cutout.

FIG. 2 is a perspective view that illustrates an example of an augment cone ("augment") 200 that can be used with the main body cone of the modular knee augment cone system 100 illustrated in FIG. 1. In the example in FIG. 2, the augment cone 200 includes a curved outside wall 205 generally hemispherical-shaped in this example, that when the augment 200 is positioned in one of the cutouts (or "slots") 105, 110, extends away from the cavity 140 creating, with the main body portion 101, an asymmetric cone-shaped structure. The cavity of the main body coin and the augment cone form a larger combined cavity. Such an augment cone 200 can be positioned in each of the cutouts 105, 110. The augment includes an edge portion 210 on opposite sides of the curved outside wall 205 each of the edge portions includes a groove 215 that is configured to receive a portion of structure of the main body on the edge of cutouts 105, 110 such that the augment 200 can be slid into a slot of the main body and held in position by the interface between the two grooves in the corresponding structure on the main body portion. FIG. 2 also illustrates a bone growth surface portion 235 on the outside surface of the augment cone 200 (illustrated as a darker surface) that is made to facilitate bone growth into the surface to hold the surface in place. In some examples, the surface structure 135 includes $P^2$. In some examples, the surface 235 is formed with a 3-D printer.

Figure 3:
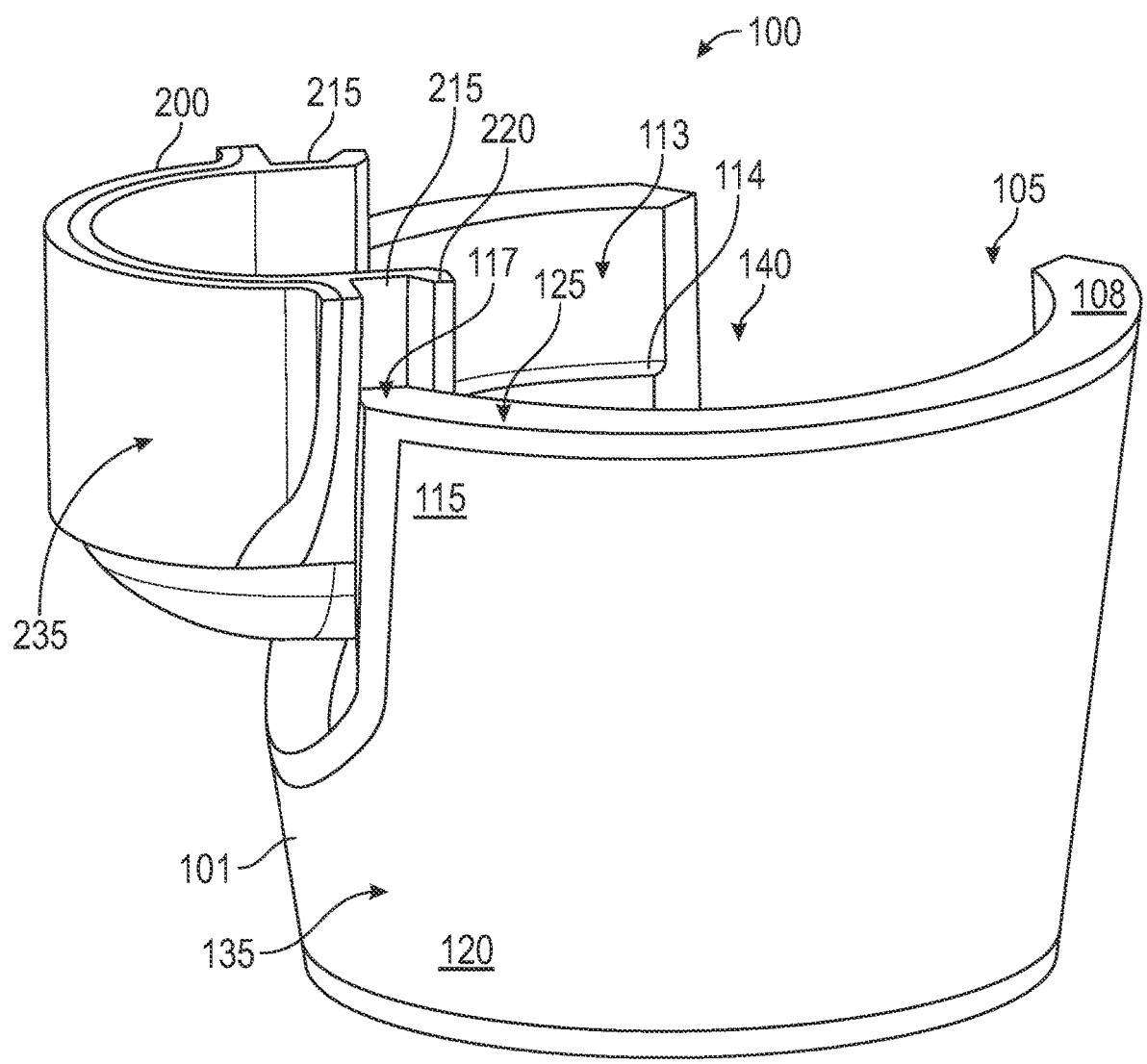
FIG. 3 is a perspective view that illustrates an example of an augment partially positioned in one of the cutouts of a main body cone, the second cutout in the main body cone not having an augment positioned therein. When the augment is seated on the cutout, the modular knee augment cone system will be an asymmetric cone. When the augment is seated in the main body cone, the side edges and lower ("distal") edges of the augment are structured to align with corresponding structure on the edges of the cutout, and the side and distal edges of the augment are positioned in close proximity to, and/or in contact with, said corresponding structure of the edges of the cutout on the main body cone.

FIG. 3 is a perspective view that illustrates an example of an augment 200 being partially positioned in one of the two cutouts of a main body cone 101, the second cutout in the main body cone shown as not having an augment cone positioned therein. As illustrated here, the augment 200 can be positioned into the slot of the main body cone by engaging the grooves 215 in the augment 200 with corresponding structure 117 on the sides of the slot of the wall 108 of the main body cone 101. When the augment 200 is fully positioned in the cutout, a portion 220 of the augment 200 is positioned adjacent to a corresponding surface 125 of the wall 108 near the cutout. The augment 200 can be held in position (at least with respective to two directions) by the interaction between the grooves 215 of the augment the corresponding attachment feature (structure) 117 of the main body cone 101. In this example, the attachment feature 117 is a dovetail that fits into the corresponding groove 215 of the augment 200. The attachment feature 117 and the corresponding groove 215 are correspondingly shaped to have a close but movable fit to allow the augment 200 to be slid into place. That is, the augment 200 is slid into the cutout from the proximal end of the main body cone 101 and is moved toward the distal end 104 until it is seated in the cutout. When the augment 200 is seated is the cutout, the modular knee augment cone system will be an asymmetric cone. When the augment is seated in the main body cone, the side edges and lower ("distal") edges of the augment are structured to align with corresponding structure on the edges of the cutout, and the side and distal edges of the augment are positioned in close proximity to, and/or in contact with, said corresponding structure of the edges of the cutout on the main body cone. The augment cone 200 can be locked into place once it is fully seated in the cutout.

Figure 4:
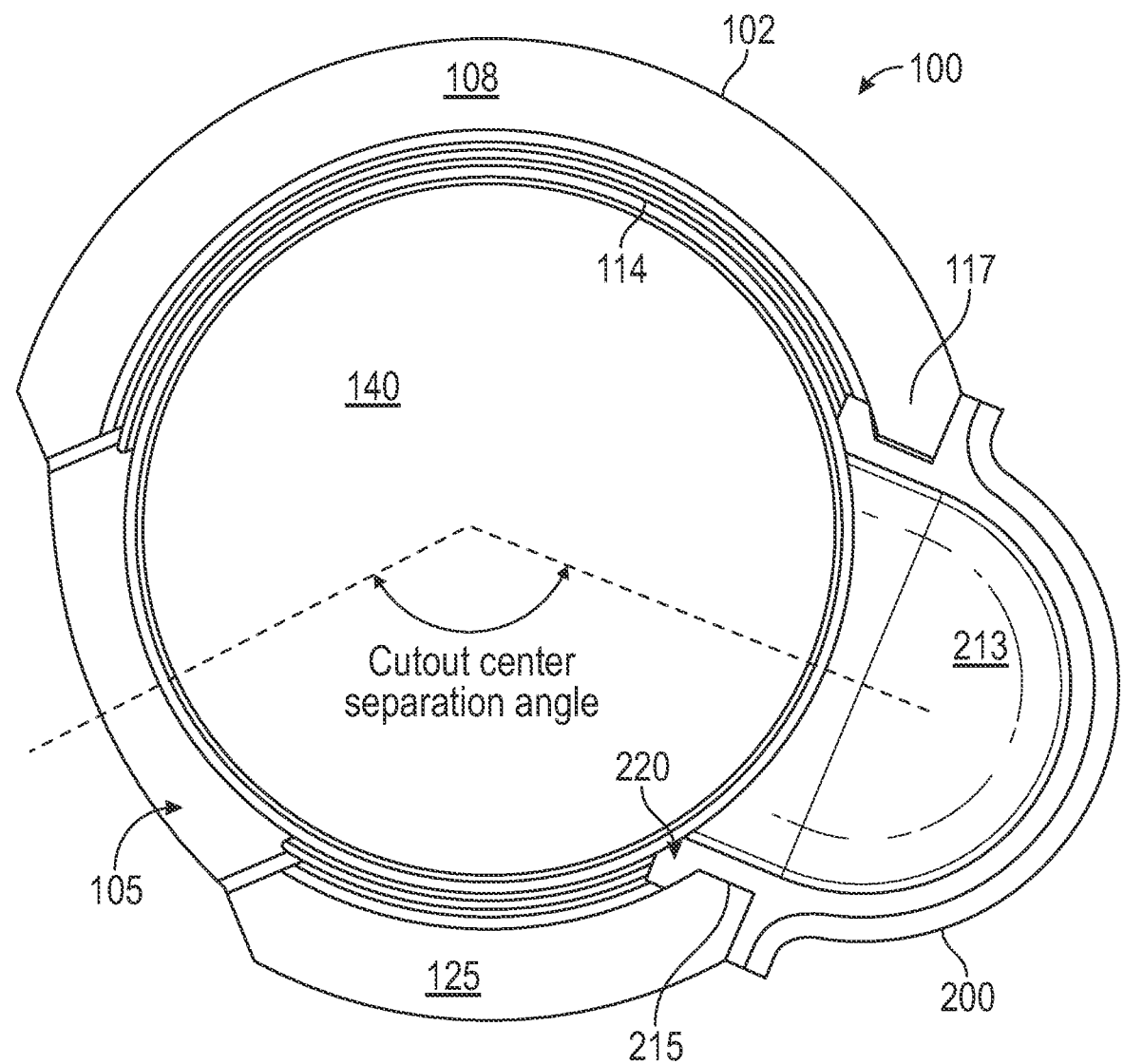
FIG. 4 is a top plan view that illustrates an example of a modular knee augment cone system having in augment positioned in a first cutout in the main body cone.
Figure 8:
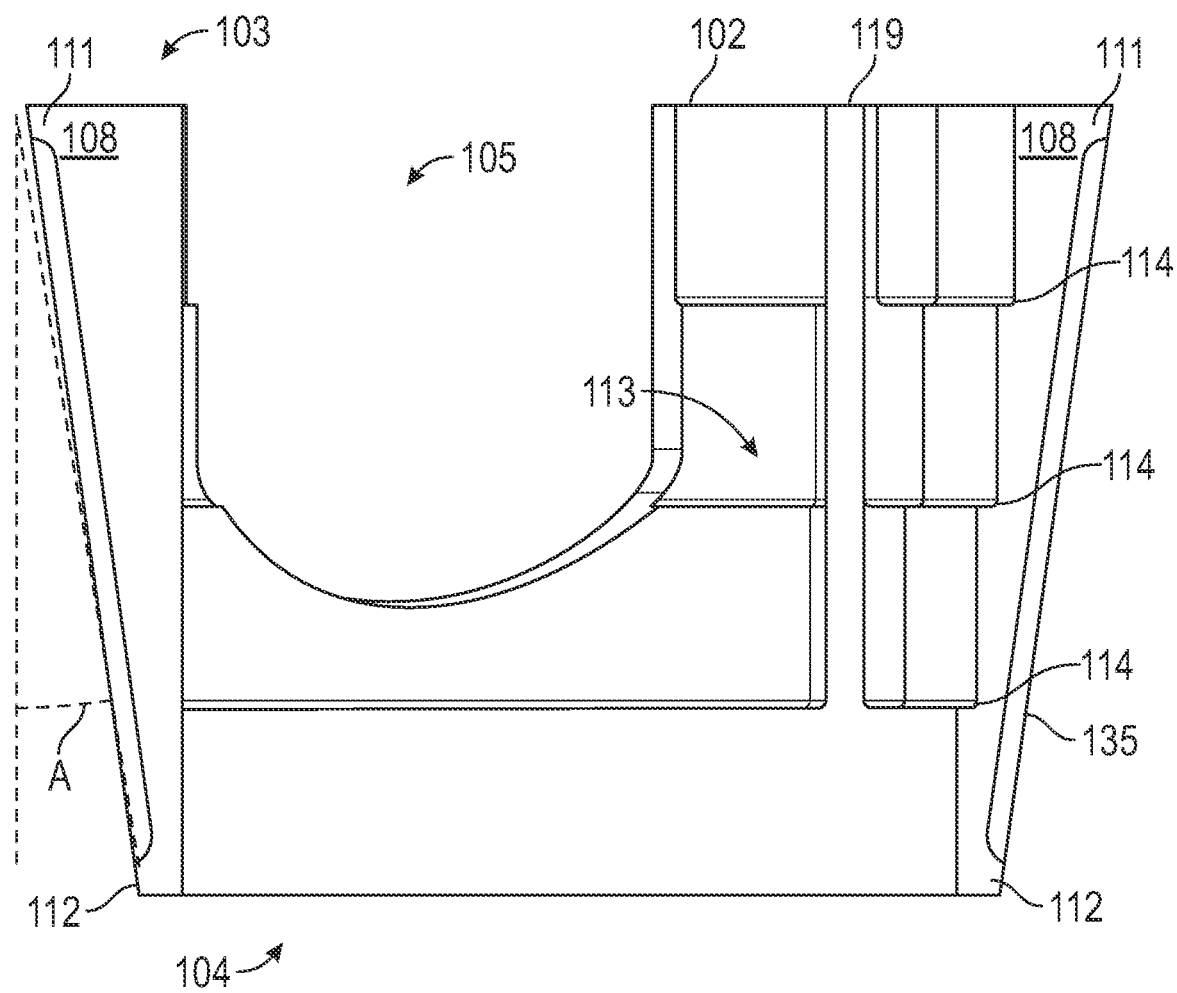
FIG. 8 is another cross-sectional side elevation view illustrating an example of a main body cone having cement mantle steps, having a bone growth coating (e.g., a porous lattice surface) on portions of the outer surface of the main body cone that is contained between an upper (proximal) ring and a lower (distal) ring, and having at least one axial rib for rotational fixation of cement, when implanted in a patient.
Figure 9:
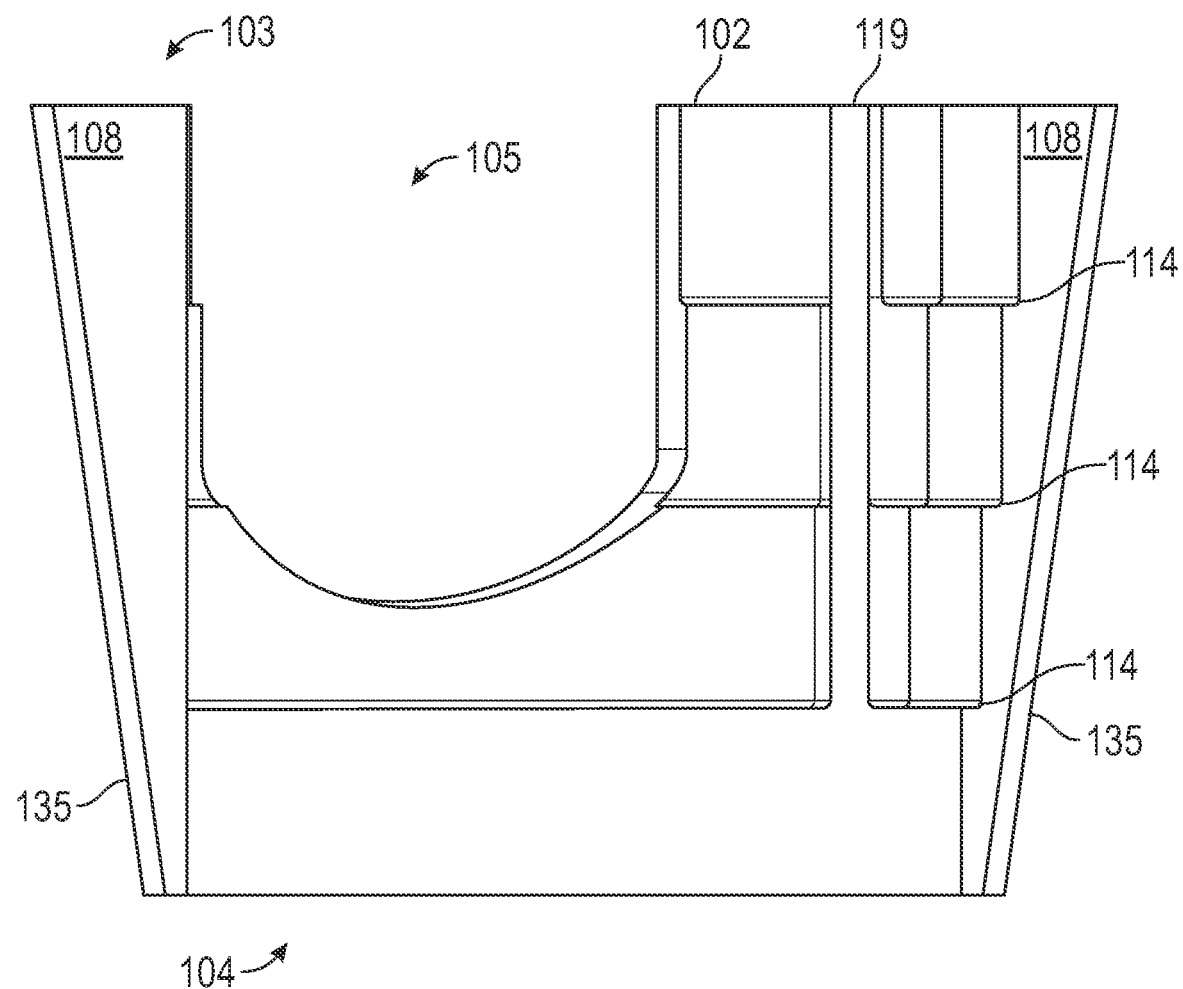
FIG. 9 is another cross-sectional side elevation view illustrating an example of a main body cone having cement mantle steps, having a bone growth coating (e.g., a porous lattice surface) on portions of the outer surface of the main body cone, and having at least one axial rib for rotational fixation of cement, when implanted in a patient. In this example, the porous lattice surface extends from an upper (proximal) surface of the main body cone to a lower (distal) surface of the main body cone.

FIG. 4 is a top plan view that illustrates an example of a modular knee augment cone system having in augment 200 positioned in a first cutout 110 in the asymmetric main body cone 102. In this illustration, although the main body cone 102 is not shown having one or more axial-aligned ribs 119, this embodiment can include such axial-aligned ribs, as illustrated in FIGS. 8, 9, and 10. Main body cones are generally preferred to have axial-aligned ribs to help prevent rotation of the main body cone around its longitudinal axis 109 (FIG. 1B). In this example, a second cutout in the main body cone 102 does not have augment positioned therein. In some example, if the use of the modular knee augment cone system only requires a single augment in a particular application, in some embodiments a second cutout in the main body may be left open. In some embodiments, the second cutout may be filled by positioning an augment or a cover plate in the unused cutout 105 in the asymmetric main body cone 102.

In this example, the second cutout is not directly opposite the first cutout, rather the position of the first and second cutouts in the main body cone 102 is asymmetric. For example, the cutout center separation angle, which is an angle formed form a line from the center of each of the first and second cutouts to the longitudinal axis 109 (FIG. 1B) of the main body cone, is less than 180 degrees. For comparison, FIG. 6 illustrates an example of a main body cone having two cutouts that are positioned directly opposite each other (e.g., cutout center separation angle equals 180°).

In an example, when the augment 200 is seated in the cutout of the main body cone an upper surface (or "proximal surface)" of the augment is coincident with an upper surface ("proximal surface") of the main body cone, and edges of the augment are positioned in close proximity to, and/or in contact with, the corresponding structure of the edges of the cutout on the main body cone which holds the augment in the main body cone. In this example the shape of the structure on the edges of the main body cone can be referred to as a "dovetail." FIG. 4 illustrates one example of the corresponding structure on the augment and on the main body cone that mates together to hold the augment 200 on the main body cone.

Figure 5:
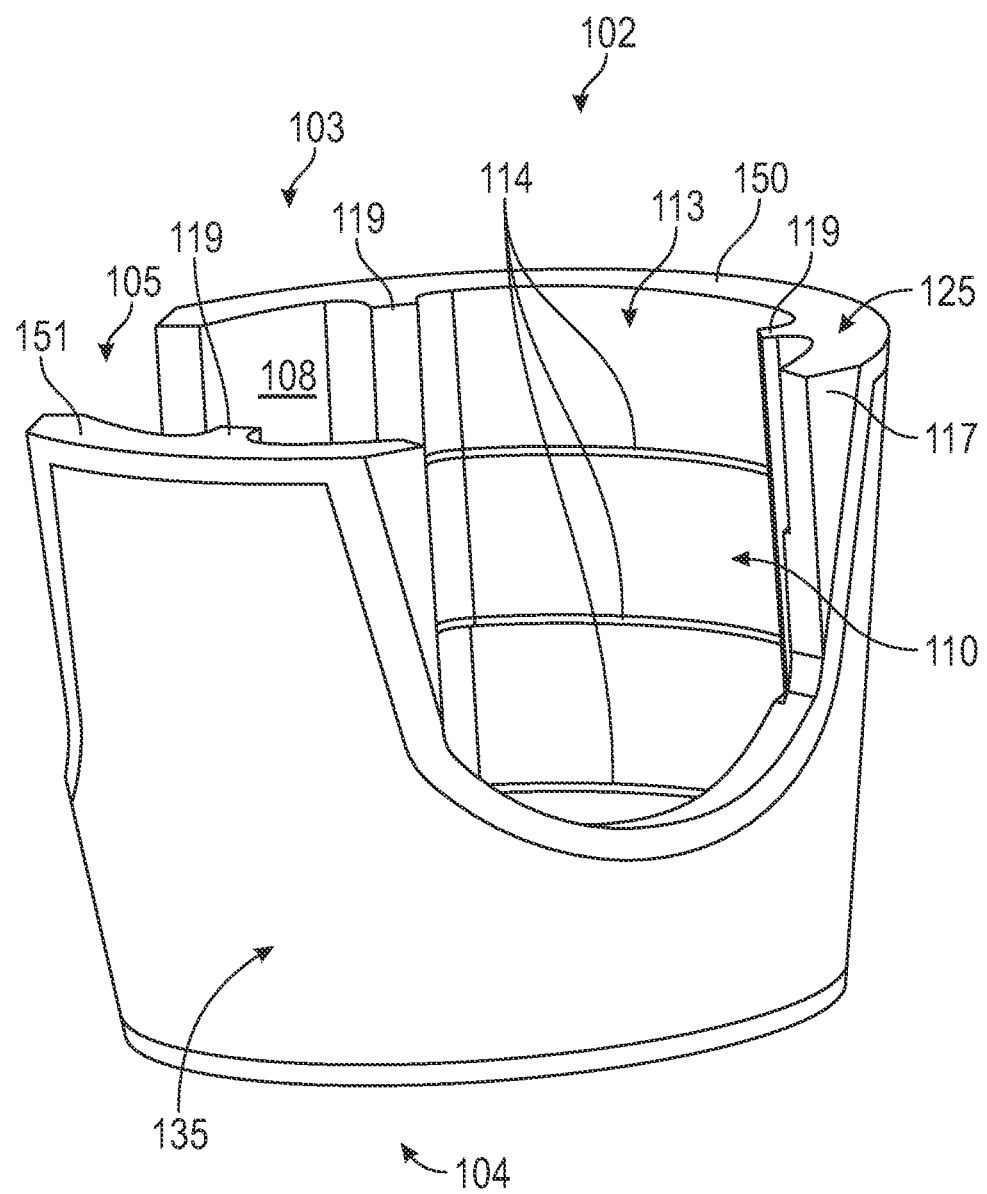
FIG. 5 is a perspective view illustrating an example of a main body cone, according to some embodiments.

FIG. 5 is a perspective view illustrating an example of an asymmetric main body cone 102. As shown in FIG. 5, the cutouts 105, 110 are arranged in the wall 108 of the main body cone 101 such that a first portion 151 of the wall 108 between the cutouts 105, 110 is shorter in distance (i.e., the circumferential run of the wall between vertical edges of the cutouts 105, 110) than a second portion 150 of the wall 108.

The main body cone 102 can include structure that protrudes from the interior wall 133 which cement can adhere to, or another structure can contact, which helps prevent axial rotation of the main body cone when it is set into a patient. In this embodiment, the main body cone 102 includes one or more ribs 119 (in this example three) that extend from the proximal end 103 to the distal end 104 of the main body cone 102. In some embodiments, the ribs 119 may be shorter in length. In some embodiments, the ribs 119 can be angled but still have a surface with a vertical aspect. The main body cone 102 also includes a plurality of cement mantel steps 114 positioned circumferentially along the inside surface 113 of the main body cone 102, for example, three cement mantel steps 114. In some embodiments, the cutouts 105, 110 positioned on opposite sides of the main body portion 102 can accommodate a baseplate keel through the cutouts (for example, see FIGS. 11 and 12).

FIG. 6 is a top plan view illustrating another example of a modular knee augment cone system having in augment 200 positioned in a first cutout 105 of a symmetric main body cone 101. In this example, the second cutout 110 in the main body cone is positioned directly opposite the first cutout 105 in the main body cone. The second cutout 110 does not have an augment positioned therein. When the augment is seated in the cutout of the main body cone, an upper surface (or "proximal surface)" 220 of the augment 200 is coincident with an upper surface ("proximal surface") 125 of the main body cone 101, and edges 210 of the augment 200 are positioned in close proximity to, and/or in contact with, the corresponding structure of the edges 106 of the first cutout 105 on the main body cone 101, which holds the augment 200 in the main body cone 101. FIG. 6 also illustrates another example of the corresponding structure on the augment 200 and on the main body portion that mates together to hold the augment on the main body portion. In this example, the augment includes an augment attachment feature 218 extending outward from an outside surface of the augment, which fits into a groove 116 in the cone wall 108 on the edge of the cutout.

Figure 7:
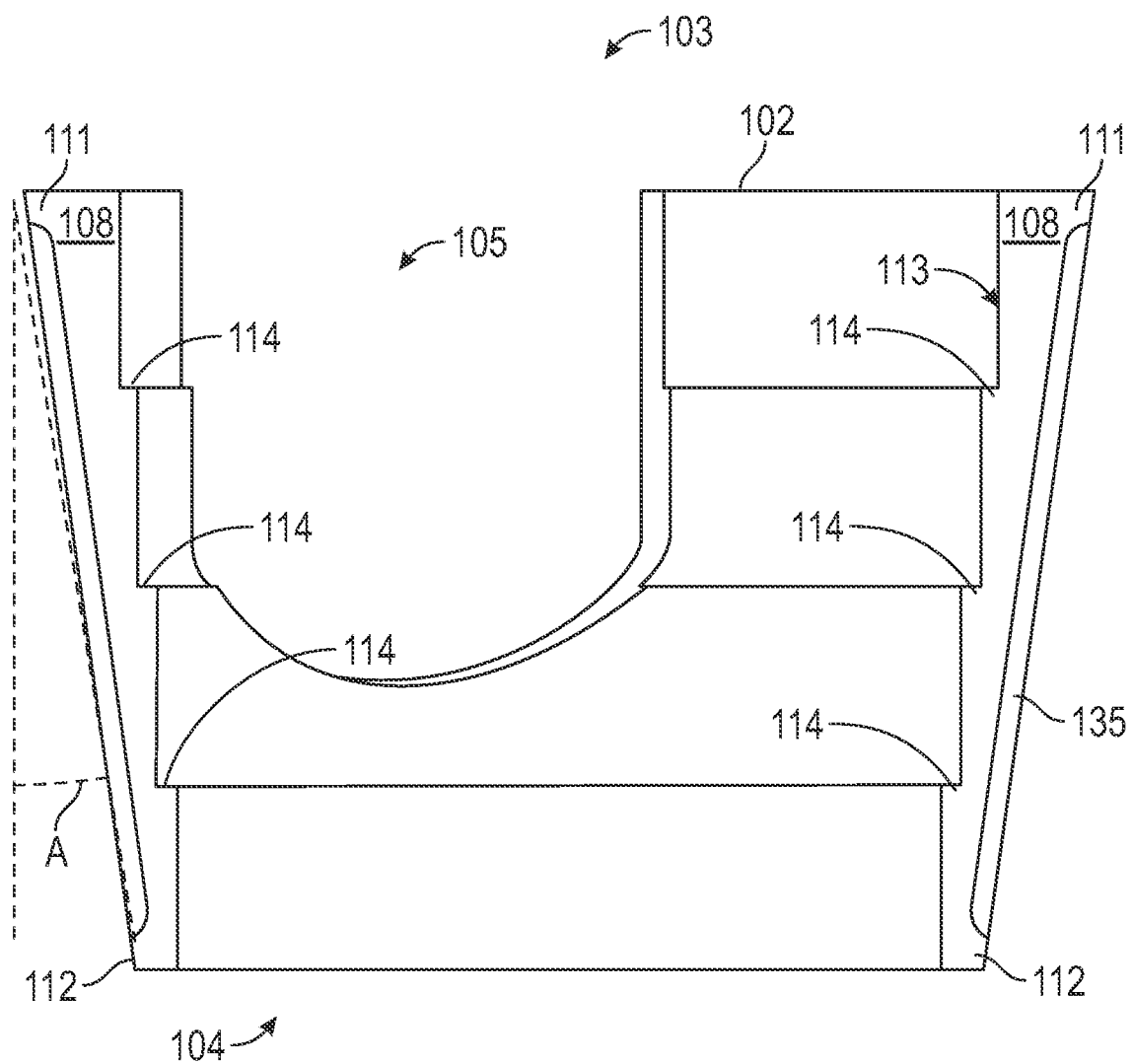
FIG. 7 is a cross-sectional side elevation view illustrating an example of a main body cone having cement mantle steps (sometimes referred to herein as circumferential ribs) and also having a bone growth coating (e.g., a porous lattice surface) on portions of the outer surface of the main body cone this is contained between an upper (proximal) ring and a lower (distal) ring.

FIG. 7 is a cross-sectional side elevation view illustrating an example of a main body cone 102. As can be seen in this view, an interior surface 113 of the main body cone 102 includes circumferential cement mantle steps 114, each step extending the interior surface 113 farther inwards towards the axial longitude of the main body cone 102 as the steps progress from the proximal end 103 to the distal end 104. This cross sectional view also shows the bone growth coating 135 on portions of the outer surface of the main body cone this is contained between an upper (proximal) ring 111 and a lower (distal) ring 112. FIG. 7 also shows that the main body cone 102 exterior walls taper inward from proximal end 103 to the distal end 104, at an angle A. In some embodiments, angle A is between 0° and 30°, for example, 1°, 2°, 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, or 30°, plus or minus 0.5°. In some embodiments, the angle A is between 5° and 15°. In some embodiments, the angle A is between 8° and 12°. In some embodiments, the angle A is between 9° and 11°.

FIG. 8 is another cross-sectional side elevation view illustrating an example of a main body cone 102. This main body cone 102 also include cement mantle steps 114, a bone growth coating 135 (e.g., a porous lattice surface) on portions of the outer surface of the main body cone that is contained between an upper ring 111 and a lower ring 112. In this example, the main body cone 120 also includes at least one axial ("vertical") rib 119 that extends a distance from the proximal end 103 of the main body cone 102 towards the distal end 104, and extends from the interior wall 113 inward towards the longitudinal axis of the main body cone. In various embodiments, the rib 119 can extend 0.5 mm, 1 mm, 2 mm, 3 mm, 4 mm, 5 mm, 6 mm, 7 mm, 8 mm, or 9 mm, plus or minus 0.5 mm. In some examples, a rib 119 extends between 1 mm and 4 mm from the interior wall 113. In various embodiments, the main body cone can include two, three or more axial ribs. The rib 119 provides a surface with a vertical aspect for cement to have purchase against, which provides resistance against a force to help prevent rotational movement of the main body cone when implanted in a patient.

FIG. 9 is another cross-sectional side elevation view illustrating an example of a main body cone 102 also having cement mantle steps 114, a bone growth coating 135 (e.g., $P^2$) on portions of the outer surface of the main body cone, and having at least one axial rib 119. In this example, the main body cone does not include an upper ring or a lower ring. Instead, the bone growth coating 135 extends on the exterior surface from the proximal end 103 the main body cone to the distal end 104 of the main body cone 102.

FIG. 10 is a perspective view illustrating an example of an asymmetric main body cone 102, a first augment 200a positioned in a first cutout 105 of the main body cone 102, and a second augment 200b positioned in a second cutout 110 of the main body cone 102. FIG. 10 also illustrates that in this example, the main body cone 102 and the first and second arguments 200a, 200b include bone growth surfaces 135 on exterior portions of these components, that is, portions of these components that will be in contact with/or adjacent to bone when the modular augment cone system is implanted in a patient. Also, the embodiment in FIG. 10 further illustrates three ribs 119 extending inward from the interior wall 113 of the main body cone 102.

Figure 11:
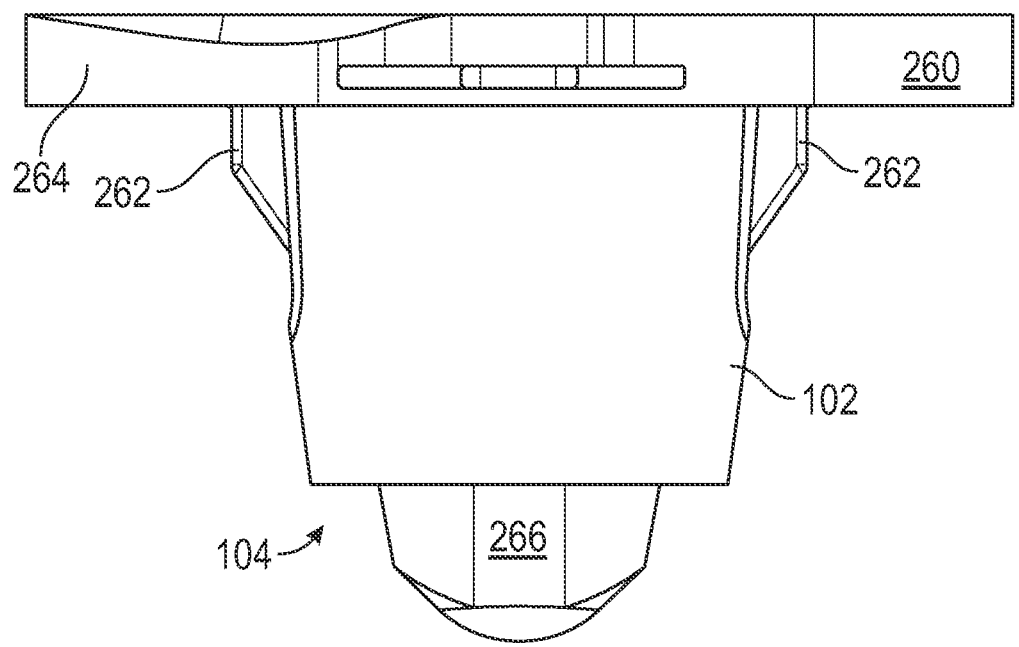
FIG. 11 is a side elevation view of an example of a main body cone having a tibial implant positioned therein, where a portion of the tibial implant extends through a first cutout and a second cutout in the wall of the main body cone.
Figure 12:
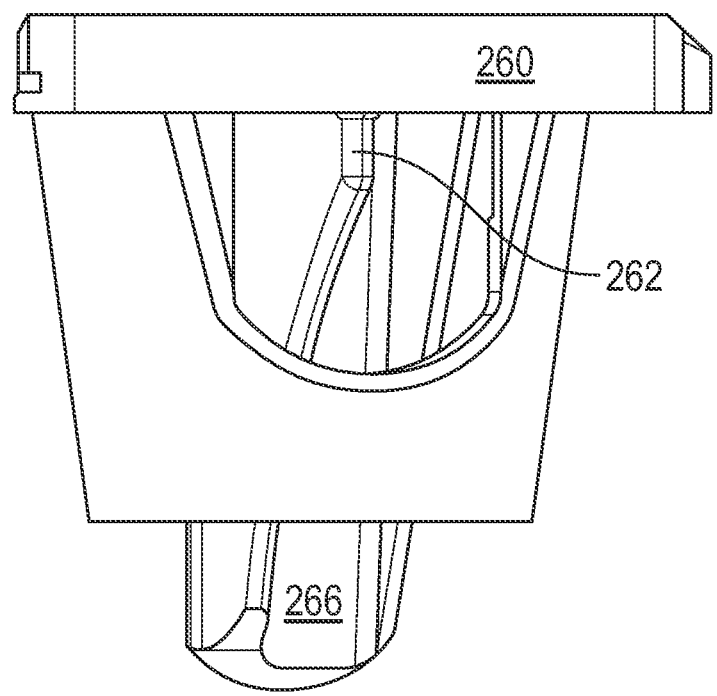
FIG. 12 is a side elevation view of the main body cone and the tibial implant illustrated in FIG. 11, where the side elevation view in FIG. 12 is axially rotated approximately 70 degrees to show a different side elevation view of these mated components.
Figure 13:
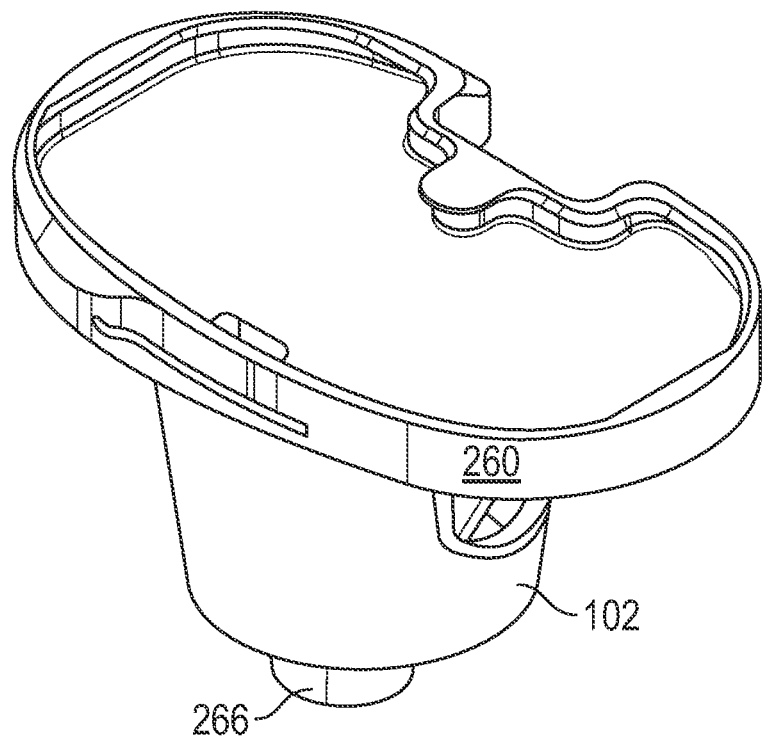
FIG. 13 is a top perspective view of the main body cone in the tibial implant illustrated in FIG. 11.
Figure 14:
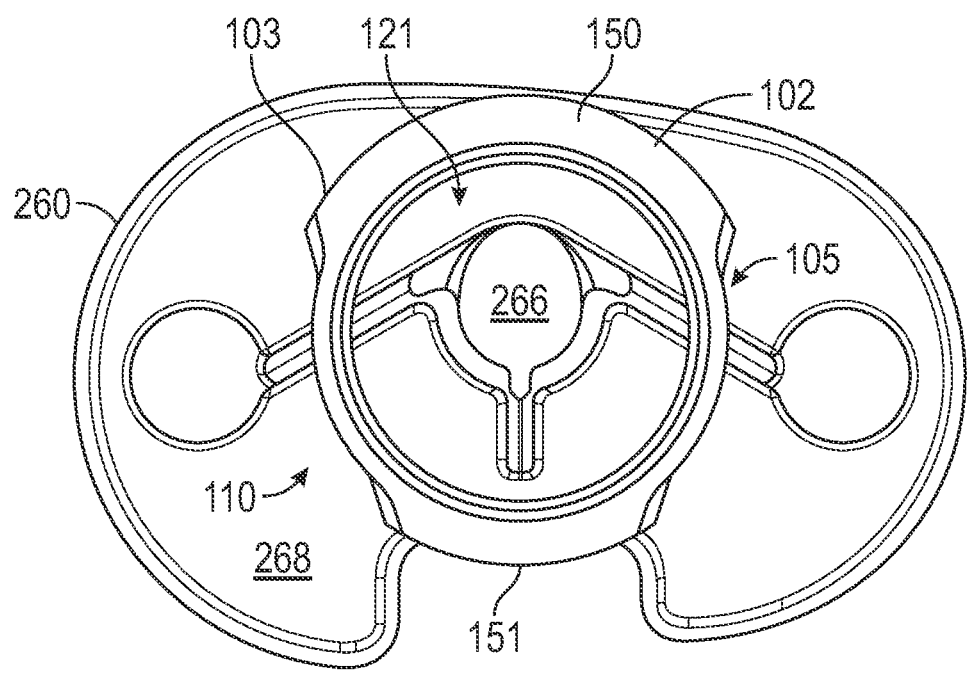
FIG. 14 is a bottom plan view of the main body cone and the tibial implant illustrated in FIG. 11.

FIGS. 11-14 illustrate an example of a main body cone 102 having a tibial implant 260 positioned therein, to illustrate the context of these two components being used together. FIG. 11 is a side elevation view of an example of a main body cone 102 having a tibial implant 260 positioned therein. The tibial implant 260 includes an upper portion 264 is positioned at the proximal end of the main body cone 102, and a lower portion 266 that extends out of the bottom of the main body cone 102, through the aperture 121 at the distal end 104 of the main body cone 102. In this example, a keel portion 262 of the tibial implant 260 extends through a first cutout and a second cutout in the walls of the main body cone. FIG. 12 is a side elevation view of the main body cone 102 and the tibial implant 260 illustrated in FIG. 11, where the side elevation view in FIG. 12 is axially rotated approximately 70 degrees to show a different side elevation view of these mated components. FIG. 13 is a top perspective view of the main body cone 102 and the tibial implant 260 illustrated in FIG. 11. FIG. 14 is a bottom plan view of the main body cone 102 and the tibial implant 260 illustrated in FIG. 11. As shown in FIG. 14 the tibial implant 260 includes a lower surface 268 that is positioned adjacent to the proximal end 103 of the main body cone 102. FIG. 14 also illustrates that the main body cone 102 is an asymmetric cone, having a long wall 150 between an edge of the first cutout and an edge of the second cutout, and having a short wall 151 between another edge of the first cutout 105 and another edge of the second cutout 110.

Figure 15:
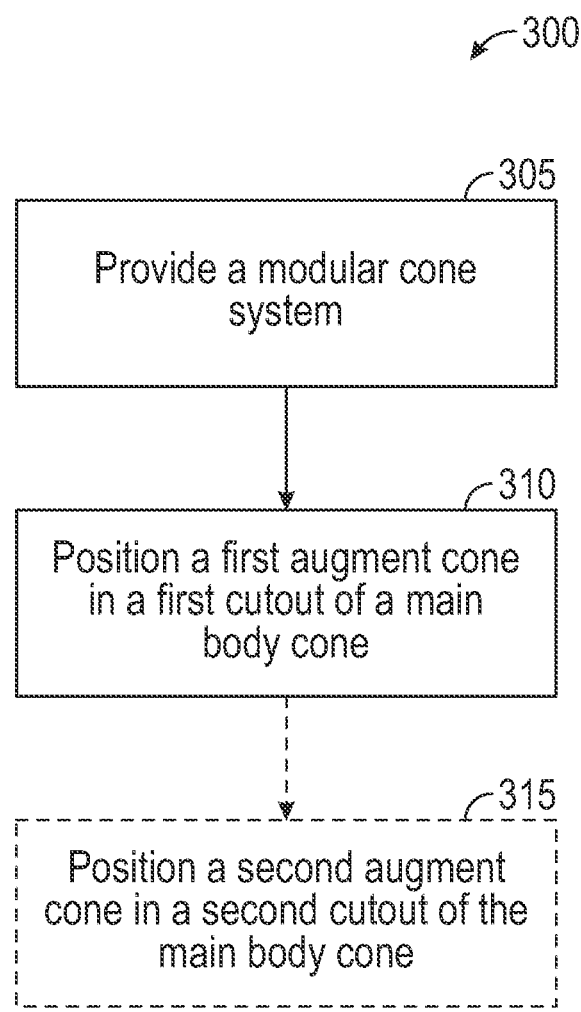
FIG. 15 is a flowchart illustrating the process for using the modular knee augment cone system described herein.

FIG. 15 is a flowchart illustrating a process 300 for using the modular knee augment cone system described herein. A knee revision procedure involves removing and replacing a partial or total knee implant with a new implant. It can be a complex surgical procedure that may require extensive preoperative planning, specialized implants and tools, including revision cones of various types based on the particular requirements of the surgical procedure. A modular knee augment cone system allows a smaller number of components to be kept on-hand, and assembled when necessary for the surgical procedure. In an example of preparing a knee to receive the modular knee augment cone system, a stem ream can be used to ream the central part of the tibia to receive a tibial component. Then a cone ream is used to ream a portion of the proximal end of the tibia to create a cavity to receive the main body cone. An augment ream can be used to create a small cavity, contiguous with the cavity for the cone, to receive the augment cone. At block 305 of process 300, a modular cone augment system is provided. The modular cone augment system includes a main body (revision) cone and at least one augment. For example, a main body cone and augment as described herein (see for example, FIG. 10). At block 310, a first augment is positioned in a first cutout of the main body cone such that it forms a portion of a wall of the main cone body. The main body cone and the augment each include a cavity, and securing the first augment into a first cutout of the main body cone forms a combined cavity defined by an interior surface of the main body cone and an interior surface of the augment, the combined cavity being larger than the cavity of the main body cone. At block 315, optionally a second augment cone is positioned in a second cutout of the main body cone. Attaching the second augment to the main body cone further increases the volume of the combined cavity of the cone/augments. The second augment can also be secured onto the main body cone using attachment structure (e.g., a screw, pin, clip, or another fastener). The assembled cone/augment system can then be placed into a patient.

Figure 16:
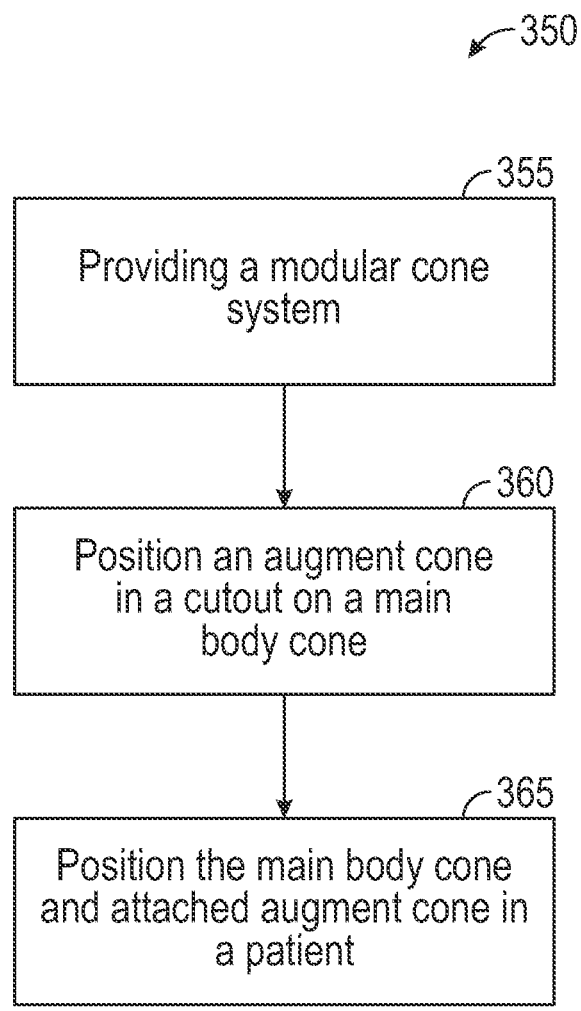
FIG. 16 is a flowchart illustrating another process for using the modular knee augment cone system described herein.

FIG. 16 is a flowchart illustrating another process 350 for using the modular knee augment cone system described herein. At block 355 of process 350, a modular cone augment system is provided. The modular cone augment system includes a main body (revision) cone and at least one augment. For example, a main body cone and augment described herein (see for example, FIG. 10). At block 360, an augment is positioned in a cutout of the main body cone such that it forms a portion of a wall of the main cone body. The main body cone and the augment each include a cavity, and securing the augment into a first cutout of the main body cone forms a combined cavity defined by an interior surface of the main body cone and an interior surface of the augment, the combined cavity being larger than the cavity of the main body cone. At block 365, the main body cone and the attached augment are positioned in a patient, for example, during a knee revision surgery.

The foregoing description details certain embodiments of the systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects of the invention should not be taken to imply that the terminology is being redefined herein to be restricted to including any specific characteristics of the features or aspects of the technology with which that terminology is associated.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Headings are included herein for reference and to aid in locating various sections. These headings are not intended to limit the scope of the concepts described with respect thereto. Such concepts may have applicability throughout the entire specification.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

The phrase "based on" does not mean "based only on," unless expressly specified otherwise. In other words, the phrase "based on" describes both "based only on" and "based at least on." Unless otherwise explicitly stated, articles such as "a" or "an" should generally be interpreted to include one or more described items. Accordingly, phrases such as "a device configured to" are intended to include one or more recited devices.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the figures may be combined, interchanged or excluded from other embodiments.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims. Applicant reserves the right to submit claims directed to combinations and sub-combinations of the disclosed inventions that are believed to be novel and non-obvious. Inventions embodied in other combinations and sub-combinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

Example Embodiments

Further examples of embodiments of the present invention are defined, without limitation, by the following Example Enumerated Embodiments (EEEs):

EEE1. A modular augment cone system, comprising: a main body cone including a proximal end, a distal end, and a cone wall extending between the proximal end and the distal end, the main body cone further including a first cutout in the cone wall, wherein a portion of the cone wall proximal to the first cutout includes a cone wall attachment feature; and a first augment cone positionable in the first cutout, the first augment cone including an augment attachment feature configured to mate with the cone wall attachment feature to attach the first augment cone into the first cutout.

EEE2. The modular augment cone system of EEE1, wherein the circumference of the proximal end of the main body cone is greater than the circumference of the distal end of the main body cone.

EEE3. The modular augment cone system of EEE1, wherein the main body cone further comprises a second cutout in the cone wall and a portion of the cone wall proximal to the second cutout includes cone wall attachment structure.

EEE4. The modular augment cone system of EEE3, wherein the first cutout is positioned opposite of the second cutout in the cone wall.

EEE5. The modular augment cone system of EEE3, wherein the first cutout and the second cutout are positioned in the cone wall such that a portion of the cone wall between a first edge of the first cutout and an adjacent first edge of the second cutout is larger than a portion of the cone wall between the second edge of the first cutout and an adjacent second edge of the second cutout.

EEE6. The modular augment cone system of EEE1, wherein the main body cone is a cross section of the main body cone parallel to a longitudinal axis of the main body cone is substantially circular.

EEE6. The modular augment cone system of EEE1, wherein the first cutout extends from the proximal end of the main body cone towards the distal end of the main body cone but does not reach the distal end of the main body cone.

EEE7. The modular augment cone system of EEE1, wherein the first cutout extends from the distal end of the main body cone towards the proximal end of the main body cone but does not reach the proximal end of the main body cone.

EEE8. The modular augment cone system of EEE1, wherein a width dimension of the first cutout along the proximal end of the main body cone is between 15 mm and 30 mm.

EEE9. The modular augment cone system of EEE1, wherein a length dimension of the first cutout along the extent of the first cutout from the proximal end of the main body cone towards the distal end of the main body cone is between 15 mm and 30 mm.

EEE10: A method of implanting a modular augment cone system, the method comprising providing the modular augment cone system of EEE1, positioning an augment cone into a first cutout of the main body cone, and implanting the main body cone.

EEE11. A method of implanting a modular augment cone system, the method comprising assembling the modular augment cone system of EEE1, by placing the first augment cone into the first cutout, and implanting the modular augment cone system comprising the main body cone and the first augment cone into a prepared space.

EEE12. A method of implanting a modular augment cone system, the method comprising providing the modular augment cone system of EEE1, and positioning a first augment cone into a first cutout of the main body cone.

What is claimed is:

1. A modular augment cone system sized and configured to receive a portion of a tibial implant, comprising:
a main body cone including a proximal end, a distal end, and a cone wall extending between the proximal end and the distal end, the main body cone further including a first cutout in the cone wall, wherein a portion of the cone wall proximal to the first cutout includes a cone wall attachment feature; and
a first augment cone positionable in the first cutout, the first augment cone including an augment attachment feature configured to mate with the cone wall attachment feature to attach the first augment cone into the first cutout,
wherein the cone wall of the main body cone includes an exterior surface comprising a porous coating,
wherein the main body cone further comprises a proximal ring structure positioned circumferentially at the proximal end of the main body cone on the exterior surface of the cone wall, and a distal ring structure positioned circumferentially at the distal end of the main body cone on the exterior surface of the cone wall, and wherein the porous coating extends between the proximal ring structure and the distal ring structure,
wherein one of the cone wall attachment feature and the augment attachment feature comprises a slot, and the other of the cone wall attachment feature and the augment attachment feature comprises an extended portion that correspondingly fits into said slot.

2. The modular augment cone system of claim 1, wherein the main body cone further comprises a second cutout in the cone wall and a portion of the cone wall proximal to the second cutout includes cone wall attachment structure.

3. The modular augment cone system of claim 2, wherein the first cutout and the second cutout are positioned in the cone wall such that a portion of the cone wall between a first edge of the first cutout and an adjacent first edge of the second cutout is larger than a portion of the cone wall between a second edge of the first cutout and an adjacent second edge of the second cutout.

4. The modular augment cone system of claim 2, wherein the modular augment cone system further comprises a second augment cone positionable in the second cutout, the second augment cone including augment attachment structure configured to mate with the cone wall attachment structure to attach the second augment cone into the second cutout.

5. The modular augment cone system of claim 1, wherein the first augment cone includes an exterior surface comprising a porous coating.

6. The modular augment cone system of claim 1, wherein the main body cone comprises one or more ribs positioned circumferentially on an interior wall of the main body cone, the one or more ribs providing surfaces that allow an adhesive to purchase against.

7. The modular augment cone system of claim 1, wherein the cone wall attachment feature comprises the slot.

8. The modular augment cone system of claim 7, wherein the attachment feature on the augment cone comprises the extended portion that fits into the slot of the cone wall attachment feature.

9. The modular augment cone system of claim 1, wherein the attachment feature on the augment cone comprises the slot.

10. The modular augment cone system of claim 9, wherein the cone wall attachment feature comprises the extended portion that fits into the slot of the attachment feature on the augment cone.

* * * * *